US006733757B2

(12) United States Patent
Patel et al.

(10) Patent No.: US 6,733,757 B2
(45) Date of Patent: May 11, 2004

(54) ADENO-ASSOCIATED VIRUS CAPSID IMMUNOLOGIC DETERMINANTS

(76) Inventors: Salil D. Patel, 21230 Homestead Rd. #10, Cupertino, CA (US) 95014; James G. McArthur, 2056 White Oaks Wy, San Carlos, CA (US) 94070

( * ) Notice: Subject to any disclaimer, the term of this patent is extended or adjusted under 35 U.S.C. 154(b) by 0 days.

(21) Appl. No.: 10/293,478

(22) Filed: Nov. 14, 2002

(65) Prior Publication Data

US 2003/0078411 A1 Apr. 24, 2003

Related U.S. Application Data

(63) Continuation of application No. 09/321,589, filed on May 28, 1999, now Pat. No. 6,498,244.

(51) Int. Cl.[7] .......... A61K 39/12

(52) U.S. Cl. .......... 424/204.1; 424/199.1; 435/235.1; 435/173.3; 435/69.3; 530/403

(58) Field of Search .......... 435/235.1, 173.3, 435/69.3, 69.1; 424/199.1, 204.1, 192.1; 530/403

(56) References Cited

U.S. PATENT DOCUMENTS 5,863,541 A * 1/1999 Samulski et al. .......... 435/69.1

OTHER PUBLICATIONS

Candace Summerford et al., "Membrane–Associated Heparan Sulfate Proteoglycan is a Receptor for Adeno–associated Virus Type 2 Virons", Journal of Virology, 72, 1438–1445 (Feb. 1998).

Candace Summerford et al., "$_{\alpha}v_{\beta}5$ Integrin: a Co–Receptor for Adeno–Associated Virus Type 2 Infection", Nature Medicine, vol. 5, p. 78–82 (Jan. 1999).

Keyun Qing et al., "Human Fibroblast Growth Factor Receptor 1 is a Co–Receptor for Infection by Adeno–Associated Virus 2", Nature Medicine, vol. 5, p. 71–77 (Jan. 1999).

Marina Moskalenko, et al., "Epitope Mapping of Human Anti–Adeno–Associated Virus Type 2 Neutralizing Antibodies: Implications for Gene Therapy and Virus Structure", Journal of Virology, vol. 74, p. 1761–1766 (Feb. 2000).

Narendra Chirmule et al., "Humoral Immunity to Adeno–Associated Virus Type 2 Vectors Following Administration to Murine and Nonhuman Primate Muscle", Journal of Virology, vol. 74, p. 2420–2425 (Mar. 2000).

Chirmule N. et al., "Immune Responses to Adenovirus and Adeno–Associated Virus in Humans", Gene Ther., Sep. 1999 6(9):1574–83. (Abstract only).

* cited by examiner

*Primary Examiner*—Laurie Scheiner
(74) *Attorney, Agent, or Firm*—Steven B. Kelber; Piper Rudnick LLP; Linda R. Judge (57) ABSTRACT

Polypeptides of adeno-associated virus (AAV) that bind to AAV antibodies or block binding of AAV to mammalian cells are described. Derivatives of peptides can be less immunogenic, enhance binding to cells, render a virus tissue specific and so on. The nucleic acid sequence encoding those derivatives can be incorporated into a capsid encoding sequence to enable a virus to express such a derivative and be less immunogenic, have enhanced transduction efficiency or be tissue specific.

10 Claims, 5 Drawing Sheets

FIG. 1

```
        → VP-1                                                          ▽LIP
  1  MAADGYLPDWLEDTLSEGIRQWWKLKPGPPPPPKPAERHKDDSRGLVLPGYKYLGPFNGLDKGEPVNEADA   70
                                        #4-5
                                                                                    →VP-2
 71  AALEHDKAYDRQLDSGDNPYLKYNHADAEFQERLKEDTSFGGNLGRAVF▽LIPAKKRVLEPLGLVEEPVKTAP  140
                                                         #16-17
                                                                      →VP-3
141  GKKRPVEHSPVEPDSSSGTGKAGQQPARKRLNFGQTGDADSVPDPQPLGQPPAAPSGLTNTMATGSGAP     210
                                  CANYON
211  MADNNEGADGVGNSSGNWHCDSTWMGDRVITTSTRTWALPTYNNHLYKQISSQSGASNDNHYFGYSTPWG    280
                                      #33
                           5-FOLD CYLINDER
281  YFDFNRFHCHFSPRDWQRLINNNWGFRPKRLNFKLFNIQVKEVTQNDGTTTIANNLTSTVQVFTDSEYQL    350
                                                #41-45
351  PYVLGSAHQGCLPPFPADVFMVPQYGYLTLNNGSQAVGRSSFYCLEYFPSQMLRTGNNFTFSYTEEDVPF    420
                           3-FOLD SPIKE LOOP 3            3-FOLD SPIKE LOOP 3
421  HSSYAHSQSLDRLMNPLIDQYLYLSRTNTPSGTTQSRLQFSQAGASDIRDQSRNWLPGPCYRQQRVSK      490
                           #58                                  #61-62
491  TSADNNSEYSWTGATKYHLNGRDSLVNPGPAMASHKDDEEKFFPQSGVLIFGKQGSEKTNVDIEKVMIT    560
561  DEEEIRTTNPVATEQYGSVSTNLQRGNRQAATADVNTQGVLPGMVWQDRDVYLQGPIWAKIPHTDGHFHP    630
631  SPLMGGFGLKHPPPQILIKNTPVPANPSTTFSAAKFASFITQYSTGQVSVEIEWELQKENSKRWNPEIQY    700
     2-FOLD DIMPLE
701  TSNYNKSVNVDFTVDTNGVYSEPRPIGTRYLTRNL                                       732
           #90
```

| MAPPED PEPTIDE | PUTATIVE EPITOPE | SUPPORTING EVIDENCE |
|---|---|---|
| DWLEDTLSEGIRQWWKLKPG<br>EGIRQWWKLKPGPPPPKPAE | EGIRQWWKLKPG | ·SITE OF "LIP" INSERTION[23]. |
| KEDTSFGGNLGRAVFQAKKR<br>NLGRAVFQAKKRVLEPLGLV | NLGRAVFQAKKR | ·SITE OF "LIP" INSERTION[23].<br>·RAVFQAKKR PROPOSED TO BIND HSPG[24]. |
| TTSTRTWALPTYNNHLYKQI | | ·CORRESPONDS TO "CANYON" FLOOR[17]. |
| GFRPKRLNFKLFNIQVKEVT<br>KEVTQNDGTTTIANNLTSTV | KEVT | ·CORRESPONDS TO "CYLINDERS" ON CAPSID SURFACE[17]. |
| TTTIANNLTSTVQVFTDSEY<br>TSTVQVFTDSEYQLPYVLGS | TSTV | ·CPV NEUTRALIZING DOG SERA BINDS TO VFTDSE[19]. |
| QMLRTGNNFTFSYTFEDVPF | | |
| YLYYLSRTNTPSGTTTQSRL | | ·CORRESPONDS TO "SPIKE" REGION[17]. |
| | | ·ANTIGENIC REGION BOUND BY MABS A3B10[18], 4AG6, 3C10 AND RABBIT SERA[19].<br>·TROPISM DETERMINING REGION IN CPV[20,21] AND AAV[22]. |
| AGASDIRDQSRNWLPGPCYR<br>QSRNWLPGPCYRQQRVSKTS | QSRNWLPGPCYR | ·CORRESPONDS TO "SPIKE" REGION[17]. |
| EIQYTSNYNKSVNVDFTVDT | | ·CORRESPONDS TO "DIMPLE" REGION[17]. |

FIG. 4

```
EGIRQWWKLKPG
NLGRAVFQAKKR
TTSTRTWALPTYNNHLYKQI
GFRPKRLNFKLFNIQVKEVTQNDGTTTIANNLTSTVQVFTDSEYQLPYVLGS
QMLRTGNNFTFSYTFEDVPF
YLYYLSRTNTPSGTTTQSRL
QSRNWLPGPCYR
EIQYTSNYNKSVNVDFTVDT
```

FIG. 5

SEQUENCE LISTING

<160> NUMBER OF SEQ ID NOS: 1

<210> SEQ ID NO 1
<211> LENGTH: 735
<212> TYPE: PRT
<213> ORGANISM: Adeno-associated virus

<400> SEQUENCE: 1

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
```

-continued

```
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

ADENO-ASSOCIATED VIRUS CAPSID IMMUNOLOGIC DETERMINANTS

This application is a continuation in part of application Ser. No. 09/321,589 filed may 28, 1999 now U.S. Pat. No. 6,498,244.

BACKGROUND OF THE INVENTION

Recombinant Adeno-associated virus (AAV) vectors are promising gene delivery vehicles because, for example, the virus is not pathogenic; the virus transduces both dividing and non-dividing cells; the virus infects a wide range of cells; and the virus integrates into the genome, which results in long term expression of the transgene.

AAV vector delivery can be obstructed by the immune response of a host to the AAV component proteins. In the case of recombinant AAV vectors, the primary target of the immune response is the capsid of the vector particle since the vectors do not encode viral proteins. For example, virus neutralizing antibodies may be generated in response to exposure to the virus.

SUMMARY OF THE INVENTION

Regions of the AAV capsid proteins were mapped to identify immunogenic sites and regions.

An object of the instant invention is to provide the amino acid sequence of such immunogenic sites and regions.

The sites can be modified, for example, to render the recombinant AAV less immunogenic or non-immunogenic; to alter the tropism of the virus; to enhance binding of the virus to a cell; and to identify analogous sites in related viruses, such as canine parvovirus.

Another object of the instant invention is to provide isolated oligopeptides that can intercede or supplant the attachment of virus and cell. Immunogenic equivalent derivatives thereof also are provided.

BRIEF DESCRIPTION OF THE DRAWINGS

FIG. 1 summarizes antibody epitope mapping of AAV. Each box represents a 15 amino acid peptide sequence from AAV VP-1 starting at MAADGY . . . and ending with . . . LTRNL. A total of 91 peptides overlapping by 5 amino acids were used. The VP-2 sequence begins with TAPGK . . . (amino acid 149, peptide 17), and the VP-3 sequence with MATGS . . . (amino acid 203, peptide 25). Blackened boxes represent detection of blocking of antibody binding by that peptide in an ELISA. Blocking peptide numbers are shown for reference above and below the grid. Serum sample designations are shown for reference to the left of the grid. Asterisks mark those sera that were positive for neutralizing antibodies.

FIG. 2 summarizes the location of the immunogenic regions of AAV on the primary sequence of the capsid proteins. Shown is the amino acid sequence of the overlapping VP-1, VP-2 and VP-3 proteins that form the AAV capsid. The arrows indicate the start point of the protein sequences of VP 1, 2 and 3. Identified immunogenic oligopeptides are underlined in bold and marked with the corresponding peptide designation. "Lip" denotes the insertion site of 4 amino acids that result in "low infectivity particle yield" mutants. The basic regions proposed to interact with heparin sulphate proteoglycan (HSGP) receptor are marked with a checkered line. The structural regions extrapolated from the canine parvovirus (CPV) structure are marked above the corresponding sequence. ▲: Key residues involved in determining tropism of CPV. Dashed box identifies the VFTDSE sequence recognized by CPV neutralizing dog serum.

FIG. 4 summarizes the sequences of immunogenic peptides identified by peptide blocking ELISA experiments. Overlapping sequences from two positive peptides are underlined and shown as putative epitopes, and overlapping sequences from three juxtaposed peptides are double underlined. The shaded area corresponds to peptides that comprise a conformational epitope. Reference 23 is Hermonat et al., infra; 24 is Summerford & Samulski, infra; 17 is Tsao et al., infra; 19 is Langereld et al., infra; 18 is Wikoff et al., infra; 20 is Chang et al., infra; 21 is Parker et al., infra; and 22 is Rutledge et al., infra.

DETAILED DESCRIPTION OF THE INVENTION

For the purposes of the instant invention, an immunogenic (or antigenic) oligopeptide (or peptide) is one that is recognized and bound by an (AAV) antibody or antiserum. The immunogenic peptide also may be one that interferes with the normal functioning of AAV, such as binding of the virus to the cell surface. The immunogenic peptide may be an epitope, a hapten or an antigenic determinant.

The phrase, amino acid, is meant to relate to the known twenty biocompatible L-amino acids that comprise proteins. The known one letter coding therefor is used herein. "Molecular Biology of the Gene", J. P. Watson et al., Benjamin Cummins, N.Y. (1987).

Also, any one peptide described herein may be used per se as provided herein or may be modified to form an equivalent immunogenic derivative thereof. The derivative may or may not have the exact primary amino acid structure of a peptide disclosed herein so long as the derivative functionally retains the desired properties of the parent peptide disclosed herein, such as binding to an AAV antibody (or antiserum) or blocking of virus binding to a cell. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer which mimics the natural conformation, charge distribution and function of the parent peptide.

Therefore, the equivalent immunogenic derivative peptide may be comprised of amino acids, nucleotides, hydrocarbons, carbohydrates and combinations thereof. For example, a derivative may be comprised of a hydrocarbon containing substituents attached thereto.

The synthesis of a derivative can rely on known techniques of peptide biosynthesis, carbohydrate biosynthesis and so on.

The selection and choice of starting materials to construct the derivative is a design choice of the artisan. As a starting point, the artisan may rely on a suitable computer program to determine the conformation of a peptide of interest. Once the conformation of peptide disclosed herein is known, then the artisan can determine in a rational design fashion what sort of substitutions can be made at one or more sites to fashion a derivative that retains the basic conformation and charge distribution of the parent peptide but may possess characteristics which are not present or are enhanced over the found in the parent peptide.

Once candidate derivative molecules are identified, the next step is to determine which derivatives retain the requisite biologic activity of the parent peptide. That can be accomplished practicing known screening methods, some of which are taught herein. For example, an ELISA wherein AAV binding antibody is immobilized to the solid phase can be used. The candidate peptides can be labeled. Alternatively, cold candidate peptides can be exposed to the solid phase antibody and then labeled AAV subsequently added thereto. Alternatively, the labeled AAV can be replaced with unlabeled AAV and a labeled AAV antibody. It should be evident that a number of permutations are possible.

As to desired characteristics of the peptide derivatives, the endpoint will depend on the eventual use of the derivative. If the derivative is to be used as a hapten for generating AAV antibody, a desirable characteristic is to have one end of the molecule carry a substituent known to be useful for conjugating molecules, for example, to a carrier molecule. Known linking molecules or substituents can be incorporated onto a peptide or peptide derivative for ready conjugation to a carrier molecule.

Another desirable feature would be resistance to peptidases. Therefore, certain amino acids of a peptide can be substituted with a replacement molecule, such as another amino acid, which would make the resulting derivative resistant to a certain peptidase.

Human sera samples positive for reactivity with AAV or monoclonal antibodies directed to AAV can be used in an immunoassay, such as an ELISA, with a capsid peptide library to identify immunogenic oligopeptides that are recognized and bound by such antibodies.

Antibodies can bind to determinants composed of amino acid residues from separated portions of the secondary amino acid sequence that are spatially juxtaposed in a folded protein (conformational epitopes) or to adjacent residues on the amino acid sequence of a protein (linear epitopes). Peptides that could block antibody binding in an ELISA generally identify linear antibody epitopes.

The AAV capsid is composed of three related proteins, VP1, VP2 and VP3 of decreasing size, present at a ratio of about 1:1:10, respectively, and derived from a single gene by alternative splicing and alternative start codon usage. Since VP-2 and VP-3 are subfragments of VP-1, a peptide library of AAV capsid protein VP-1 can be used to identify immunogenic oligopeptides of VP-2 and VP-3 as well. For example, a library composed of, for example, 15-mers overlapping by, for example, 5 amino acids, and thus containing all possible 10-mers of the 735 amino acid sequence of VP-1 can be used.

Figure 1:
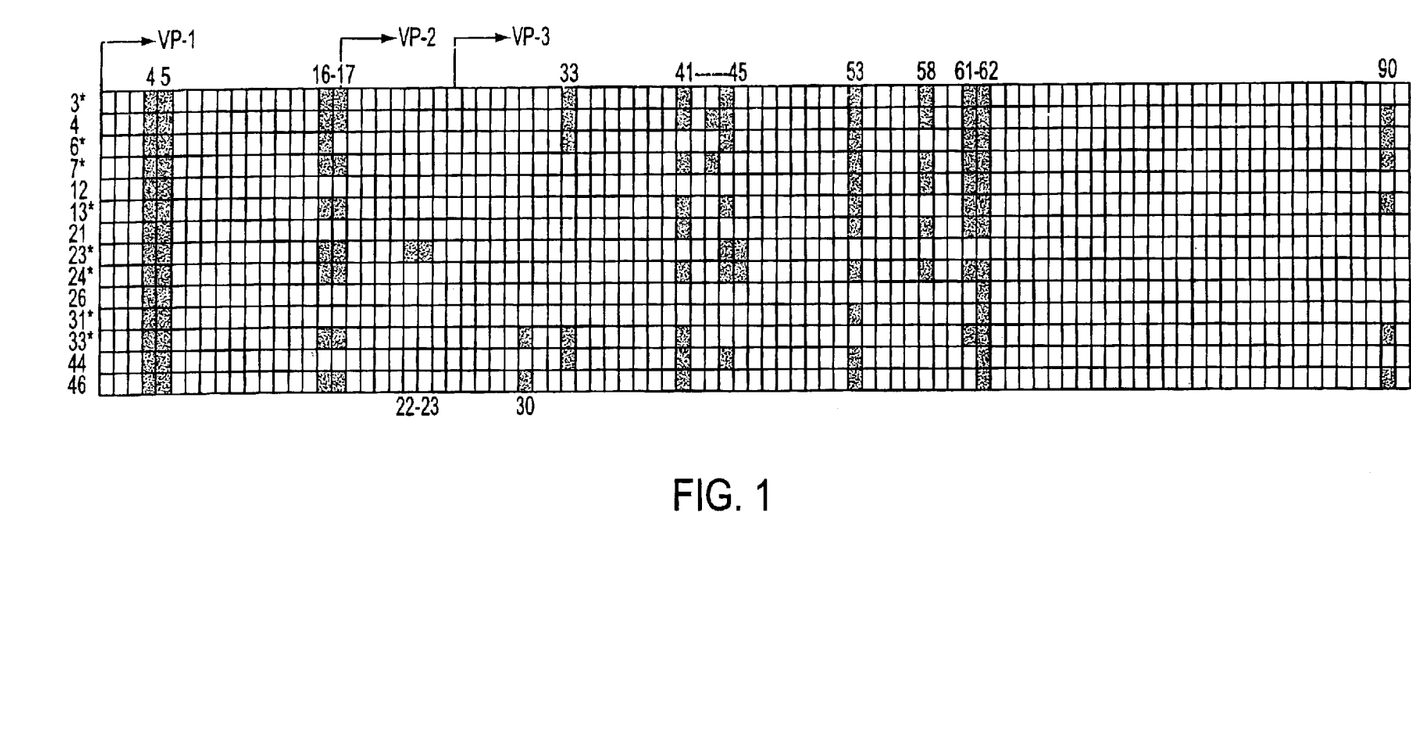
Figure 2:
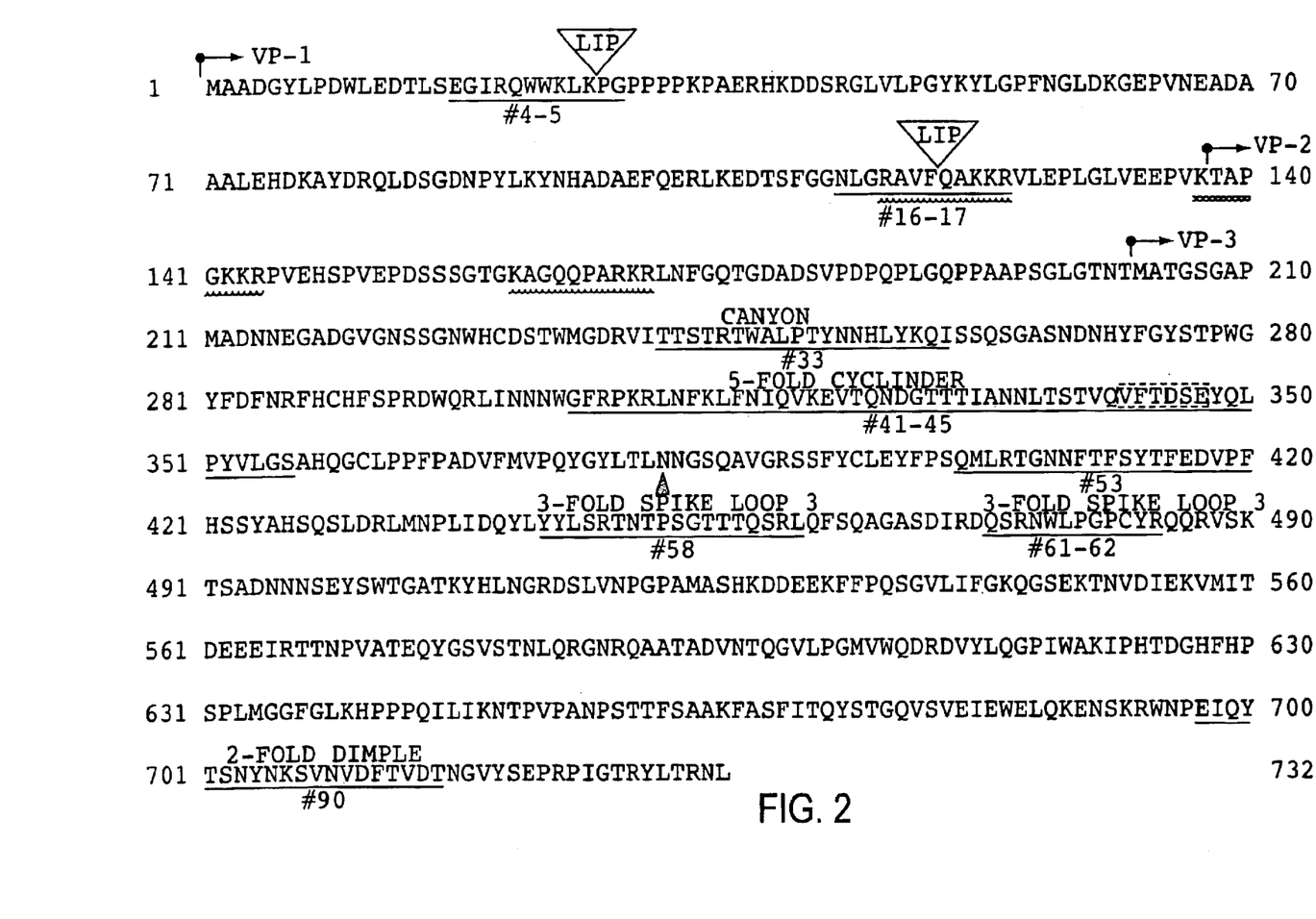
Figure 4:
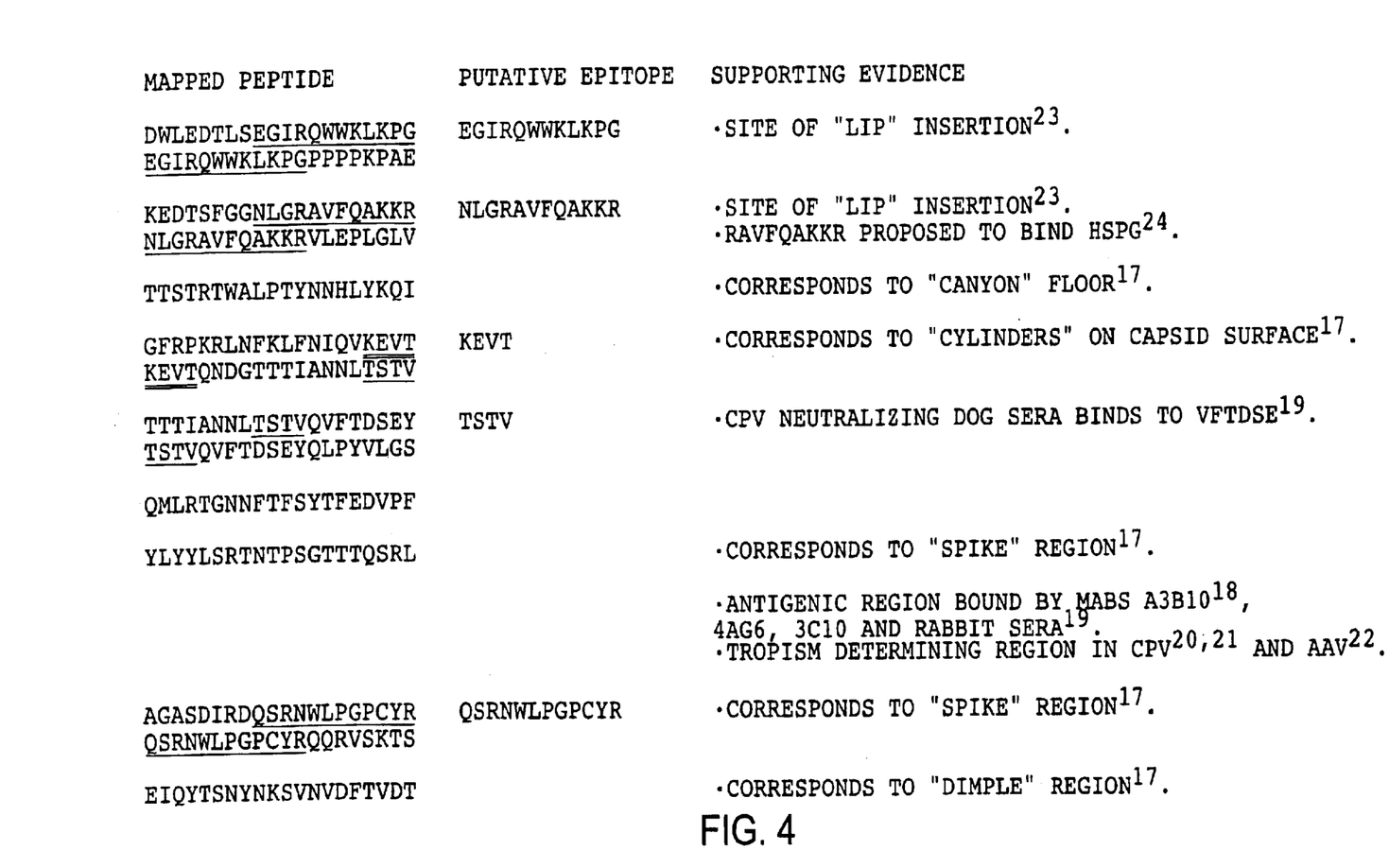
Figure 5:
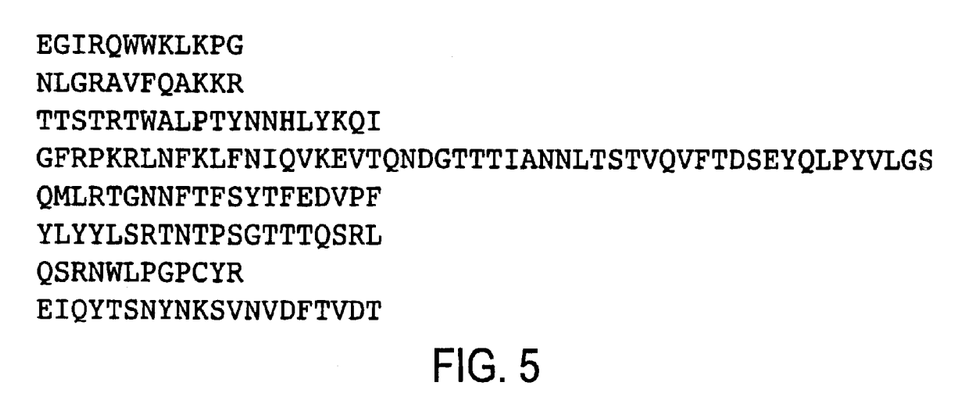
FIG. 5 depicts stretches of amino acids that comprise immunologic determinants.

By practicing that strategy, seven regions of immunogenic sequences were identified in the majority of human serum samples reactive with AAV that were tested, as depicted in FIG. 1 and listed in FIGS. 2, 4 and 5.

Some peptides blocked antibody binding in all seven patient samples tested (e.g., peptides 4 and 5), some in the majority of patient samples (e.g., peptides 16, 17, 61 etc.) and some in only a few patient samples (e.g., peptide 33).

Several tandem peptide pairs or triplets blocked binding presumably due to a shared, overlapping epitope sequence.

The neutralizing antibody samples can be used to recognize AAV conformational epitopes.

A pool of 14 peptides (peptides 4, 5, 16, 17, 33, 61, 62, 41, 43, 44, 45, 53, 58 and 90) that blocked antibody binding in the ELISA using the human serum samples was tested to detect any relationship between and among peptides. The pool inhibited the neutralizing effect of seven different neutralizing positive sera (Ser3, Ser6, Ser7, Ser13, Ser23, Ser24 and Ser31) to the same extent.

The peptides also reduced AAV uptake, suggesting that the series of peptides contain mimetic sequences involved in the binding of AAV to the cognate receptor thereof on the cell surface. The pool then was divided into two smaller pools of 7 peptides each. Pool 1 contained peptides 4, 5, 16, 17, 33, 61 and 62; and pool 2 contained peptides 41, 43, 44, 45, 53, 58, and 90. Those combinations maintained juxtaposed peptides that likely contain a single conformation epitope or determinant within the same pool.

Pool 2 partially reversed the neutralizing effect. A control "negative pool" of 7 peptides (peptides 7, 8, 9, 10, 11, 12 and 85) showed no inhibition. Removal of peptide 90 from pool 2 had no effect on inhibition implying the core neutralizing pool of peptides to be composed of peptides 41, 43, 44, 45, 53 and 58. The same pattern was observed with five serum samples (Ser3, Ser6, Ser7, Ser23, and Ser24) and also with a neutralizing anti-AAV mouse monoclonal antibody, A20. (Wistuba et al., J. Virology 69, 5311–5319, 1995; 71, 1341–1352, 1997).

The blocking of a neutralizing monoclonal antibody suggests that the identified peptide sequences reconstitute a single conformational epitope. As shown in FIG. 4, an overlap analysis and the expendability of peptide 42 point to sequences KEVT and TSTV as key residues within the conformational epitope.

The immunogenic peptides identified would be expected to be on exposed surfaces of the AAV capsid since neutralizing antibodies generally bind to the virus surface to prevent virus binding to cellular receptors and subsequent viral uptake into the cell.

There is a high structural conservation between AAV and canine parvovirus (CPV), which typifies parvovirus in general. Contact points of AAV with the receptors thereof now are identified (Summerford & Samulski, infra; Summerford et al., Nat. Med. 5, 78–82, 1999; Qing et al., Nat. Med. 5, 71–77, 1999).

The alignment of CPV VP-2 with the AAV sequence (beginning at amino acid 176) and superimposition on the CPV structure thereon (Chapman et al., Virology 144, 491–508, 1993) allow the structural location of the antigenic sites identified herein to be extrapolated between the species.

The three-dimensional structure of CPV has been determined (Tsao et al., Science 251, 1456–1464, 1991). The virus is a T=1 icosahedral structure (depicted in FIG. 3) composed of 60 subunits of VP-1, VP-2 and VP-3 and is characterized by several exposed structural regions that are referred to using previously reported nomenclature (Chapman et al., Tsao et al., supra).

Figure 3:
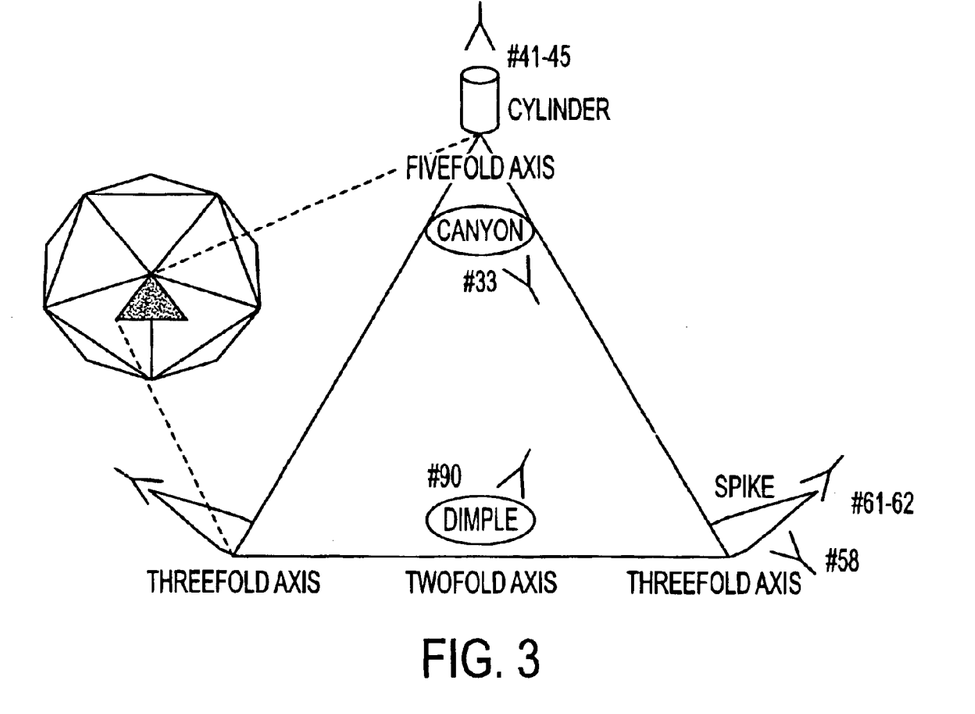
FIG. 3 is a schematic representation of the parvovirus structure, adapted from Langeveld et al., infra, that shows the approximate structural locations of the immunogenic oligopeptides. The icosahedral structure (left) is composed of 60 icosahedral units (shaded triangle) formed by VP1, VP2 and VP3. The expanded triangle represents one icosahedral unit.

Assuming AAV has a structure similar to CPV, as summarized in FIGS. 2 and 3, several of the B cell determinants identified correspond to exposed regions of AAV.

A "cylinder" structure protrudes from each five-fold axis and is encircled by a "canyon". Each three-fold axis also has a protruding "spike" formed by 4 loops and each two-fold axis contains a depression termed a "dimple".

Peptide 33 lies in the canyon and peptides 41–45 are located on the cylinder structure. Peptides 58, 61 and 62 are found on the spike region and peptide 90 is located at the two-fold dimple. In addition, peptide 58 binds monoclonal antibodies (Wikoff et al., Structure 2, 595–607, 1994; Langeveld et al., J. Virology 67, 765–772, 1993) and rabbit sera. Furthermore, that region contains critical residues that have been shown to determine the tropism of CPV (Chang et al., J. Virology 66, 6858–6867, 1992; Parker et al., J. Virology 71, 9214–9222, 1997) and to determine different AAV subtypes (Rutledge et al., J. Virology 72, 309–319, 1998).

AAV mutants that produce 0.01 to 1% of the normal virus yield have been described (Hermonat et al., J. Virology 51, 329–339, 1984). The low infectious particle yield (lip) mutants were generated by random insertion of 8 or 9 base pair sequences which results in an in frame addition of 4 amino acids. Two of the three lip mutations map to and disrupt the peptides described herein, suggesting that those regions form surface exposed domains that are critical for virus binding and uptake.

Furthermore, one of several regions of basic amino acid motifs that have been identified and proposed to interact with the glucosaminoglycan component of HSPG of AAV (Summerford & Samulski, J. Virology 72, 1438–1445, 1998) forms part of peptides 16 and 17 (FIG. 2).

The peptides identified herein are bound by AAV neutralizing antibodies and inhibit binding of viruses to cells of a host.

As taught hereinabove, the actual amino acid sequence of any one peptide can be varied to yield an immunogenic derivative, for example, by removing one or more amino acids; adding one or more amino acids; substituting one or more amino acids; or any combination thereof. Moreover, the peptide can be mimicked by another molecule or polymer, such as a carbohydrate or a hydrocarbon. The determinative factor is whether the derivative of a specific peptide retains the distinguishing characteristics thereof, such as, binding to an AAV antibody (or antiserum) or blocking binding of AAV to a host cell.

A reduction in the distinguishing characteristic of up to 50% of that observed for the parent peptide is tolerable in the derivative, particularly if the derivative has other desirable characteristics, such as degradation resistance. Thus, for example, if a peptide is observed to bind antibody to a certain extent, or is observed to inhibit binding of AAV to a cell at a certain level at a certain concentration, a decrease of up to 50% of the observed value of the parent molecule can be found in a derivative within the scope of the instant invention A suitable way to determine if a derivative is usable in the practice of the instant invention is to use known methods as taught herein, or equivalent methods, which demonstrate the immunogenicity and function of a peptide of the AAV capsid proteins. Therefore, an immunoassay, such as an ELISA, RIA, neutralization assay and so on can be used. Also, an assay that demonstrates binding of virus to a cell can be practiced. Those such assays can afford the necessary comparison of a derivative and the parent peptide.

As taught herein, suitable derivatives are those which are found to carry desirable characteristics. For example, the oligopeptides may be manipulated to find derivatives that are less immunogenic or not immunogenic. When such derivatives are identified, the changes can be configured into the capsid coding sequence of a recombinant AAV using known techniques resulting in the production of virus which will not evoke a strong or any host immune response thereto.

Also, alteration of an oligopeptide may influence the binding of a virus to a cell. A desirable characteristic would be a change that enhances binding of virus to a cell. Another desirable characteristic would be change that influences the tropism of the virus. Controlling the tropism of the virus would enable tissue-specific targeting of the viral vector. Again, once the desired change is identified, the coding sequence of the capsid proteins can be modified so that the expressed capsid proteins of the recombinant virus carry the same desirable change found in any one derivative.

Also, as noted herein, the parvoviruses share a similar structure and function. Therefore, identification of immunogenic peptides in one species of parvovirus will enable identification of similar sites in other parvoviruses, as noted herein.

The oligopeptides of interest will find use in nitro methods, such as purification schemes. For example, oligopeptides that inhibit binding of virus to receptor can be used as competitive inhibitors to release bound virus in an adsorption-type assay. The same may apply if antibody were used as an immunoadsorbent, an oligopeptide could be used to elute bound virus from a solid support to which AAV antibody is immobilized.

The peptides, and particularly certain immunogenic derivatives thereof, may find use in vivo. Also, the sequence of modified peptides can be incorporated into the capsid sequence of a recombinant AAV by subcloning a polynucleotide encoding such a modified peptide into the nucleic acid encoding a capsid protein. The polynucleotide can replace the sequence found in the wild-type capsid nucleic acid. Methods for manipulating pieces of nucleic acids are known. Methods for making recombinant AAV are known in the art. Moreover, methods for administering peptides or AAV are known in the art. The amounts of peptides or rAAV to be administered to a host in need of treatment will have been determined for the unmodified AAV. Because the peptides of the instant invention, if the sequences therefor are incorporated into a virus, would be, for example, less immunogenic, a lower dosage can be used. An artisan would determine the appropriate new dosage by extrapolating from pre-clinical data or clinical data. Regarding the dosing of peptides, again the artisan would follow accepted methods of extrapolating from pre-clinical and clinical studies. As some derivatives may be stable, that is, resistant to degradation in the host, the long term dosing would have to be adjusted to take those charasteristics into account. The amount of peptide or virus in the host can be determined by sampling, for example, a blood specimen or a tissue biopsy, and determining the levels thereof therein using known techniques, such as those taught therein.

Preclinical and clinical data are used in formulating a range of dosing for human use. The dose may vary depending on the form used and the route of administration. The artisan will know how to make necessary adjustments.

Pharmaceutical compositions comprising AAV may be formulated as known using physiologically acceptable carriers, diluents or exicipients.

The AAV preparations are formulated for administration by any of a variety of routes, such as, inhalation, oral, buccal, parenteral or rectal administration.

For administration by inhalation, the AAV can be delivered as an aerosol spray from pressurized packs or a nebulizer, with the use of a suitable propellant.

For oral administration, the pharmaceutical compositions may take the form of, for example, tablets, lozenges or capsules prepared by conventional means with pharmaceutically acceptable excipients, such as binding agents; fillers; lubricants; glidents; disintegrents; or detergents. The tablets may be coated.

Liquid preparations may take the form of, for example, solutions, syrups or suspensions, or a dry product for constitution with water or other suitable vehicle before use. The liquid preparations can contain pharmaceutically acceptable additives such as suspending agents; emulsifying agents; non-aqueous vehicles; and preservatives. The preparations may also contain buffer salts, flavoring, coloring and sweetening agents.

Preparations for oral administration may be suitably formulated to provide controlled release of the active compound.

The AAV may be formulated for parenteral administration by injection, for example, by bolus injection or infusion. Formulations for injection may be presented in unit dose, for example, in ampoules or in multi-dose containers, with an added preservative. The compositions may take such forms as suspensions, solutions or emulsions in oily or aqueous vehicles as needed, and may contain additives such as suspending, stabilizing and dispersing agents. Alternatively, the active ingredient may be in a powder or a lyophilized form for constitution with a suitable vehicle, for example, sterile pyrogen-free water, before use.

The AAV also may be formulated for long term release. Such long acting formulations may be administered by implanation (for example, subcutaneously or intramuscularly) or by intramuscular injection. Thus, for example, the therapeutic compounds may be formulated with suitable deposition material, for example, an emulsion.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration.

The invention now will be exemplified in the following non-limiting examples.

EXAMPLE 1
Construction and Production of AAV Vectors

AAV vectors expressing green fluorescent protein (GFP) (Klein et al., Exp. Neurol. 150, 183–194, 1998), β-galactosidase (McCown et al., Brain Res. 713, 99–107, 1996) and HFIX were constructed and generated using known techniques, such as taught in Snyder et al., (Nat. Genet. 16 1997 270–272). Titers were determined by dot blot analysis.

EXAMPLE 2
Detection of Anti-AAV Antibodies Using ELISA

Ninety-six well MaxiSorp flat surface Nunc-Immuno plates were coated with $5 \times 10^7$ particles of AAV in 1000 μl/well of 0.1 M carbonate buffer pH 9.6, incubated overnight at 4° C. and washed twice with washing buffer from an AMPAK amplification kit (DAKO, Carpenteria, Calif.). After blocking with 3% BSA in washing buffer for 2 hours at room temperature, the plates were washed once and incubated for 1 hour at room temperature with donor serum at 1:100 dilution in washing buffer, 1% BSA in a total volume 100 μl/well. Next, the plates were washed 5 times and AP conjugated mouse anti-human antibodies (Zymed, San Francisco, Calif.) were added at 1:800 dilution in washing buffer, 1% BSA, 100 μl/well. The plates were incubated for 1 hour at room temperature and washed with washing buffer 4 times. For color development and further amplification of the signal, the AMPAK amplification kit was used. Absorbance was measured at 490 nm.

EXAMPLE 3
Detection of Neutralizing Anti-AAV Antibodies 293 cells were seeded in a 24 well plate at a density of $1 \times 10^5$ cells per well, in 1 ml of IMDM media (JRH). The cells were allowed to adhere for 2 hours at 37° C. The media then was removed by aspiration before $6 \times 10^6$ particles of adenovirus dl309 (Ferrari et al., J. Virology 70, 3226–3234, 1996), were added in a final volume of 200 μl per well. The cells were incubated further at 37° C. for 1 hour and then washed twice in the same media before the following mix was added. AAV-GFP (1 μl=$5 \times 10^8$ total particles or $9 \times 10^6$ transducing units) virus was incubated with serum sample diluted in PBS for 2 hours at 4° C. in a total volume of 25 μl. The final dilution of the test serum was 1:100 or 1:1000. The mix was added to the washed cells in a final volume of 200 μl, and incubated for 1 hour at 37° C. About 400 μl of media then were added to each well and cells were incubated overnight. Cells were collected, washed in PBS/BSA (1%), and analyzed by FACS. The % inhibition was calculated using a "no antibody" control sample as a reference. Another control was anti-AAV guinea pig sera that showed maximal inhibition.

EXAMPLE 4
Epitope Mapping of Anti-AAV Antibodies

A set of 91 overlapping peptides (15mers) spanning the entire 735 amino acid AAV-VP1 capsid protein sequence (Genbank # AF043303) were synthesized using the PIN synthesis strategy (Chiron Mimotopes, Clayton, Australia). The peptide sequences overlap by 5 amino acids thus generating all possible 10mers of VP-1. Two control peptides also were synthesized to verify purity and assess yield. Peptides were resuspended in PBS at a concentration of 5 mg/ml and stored at −20° C.

ELISA analysis was performed in the presence of 1 μl (corresponding to a final concentration of approximately 20 μM) of individual peptides or 10 μl peptide pools which were present at the antibody incubation stage. Similarly, 1 μl of each peptide was added to the 25 μl antibody-AAV-GFP mix in the neutralizing assay to assess the ability to block the binding of neutralizing antibodies to AAV-GFP.

All references cited herein are incorporated by reference in entirety.

It will be readily evident to the artisan that various changes and modifications can be made to the teachings herein without departing from the spirit and scope of the instant invention.

We claim:

1. An isolated and modified adeno-associated virus (AAV) capsid protein comprising epitopes, wherein said epitopes are residues 17–28, 113–124, 241–260, 305–356, 401–420, 443–460, 473–484 and 697–716 of SEQ ID NO: 1, and wherein one or more of said epitopes is modified and said modified epitope does not bind an AAV antibody that binds to unmodified AAV capsid protein.

2. An AAV particle comprising said modified capsid protein of claim 1.

3. The particle of claim 2, wherein said antibody is a neutralizing antibody.

4. An isolated polypeptide consisting essentially of an oligopeptide, which is a portion of an adeno-associated virus (AAV) capsid protein that specifically binds to an antibody, wherein said antibody binds specifically to AAV, and further wherein said oligopeptide is selected from the group consisting of amino acid residues 17–28, 113–124, 241–260, 305–356, 401–420, 443–460, 473–484 and 697–716 of SEQ ID NO: 1.

5. The isolated polypeptide of claim 4, wherein said polypeptide blocks binding of an anti-AAV capsid antibody to AAV.

6. The isolated polypeptide of claim 4, wherein said polypeptide blocks the effect of a neutralizing antibody on AAV.

7. The isolated polypeptide of claim 4, wherein said polypeptide inhibits binding of AAV to a mammalian cell.

8. A recombinant AAV particle comprising a modified oligopeptide selected from the group consisting of amino acid residues 17–28, 113–124, 241–260, 305–356, 401–420, 443–460, 473–484 and 697–716 of SEQ ID NO: 1, wherein when said oligopeptide is incorporated into the capsid of said AAV particle, the tropism of said AAV particle is altered relative to an AAV particle lacking said modified oligopeptide.

9. A recombinant AAV particle comprising a modified oligopeptide selected from the group consisting of amino acid residues 17–28, 113–124, 241–260, 305–356, 401–420, 443–460, 473–484 and 697–716 of SEQ ID NO: 1, wherein an AAV antibody that binds specifically to an unmodified oligopeptide does not bind to said particle.

10. A recombinant AAV capsid protein comprising a modified oligopeptide selected from the group consisting of amino acid residues 17–28, 113–124, 241–260, 305–356, 401–420, 443–460, 473–484 and 697–716 of SEQ ID NO: 1.

* * * * *